(12) United States Patent
Lasser

(10) Patent No.: US 6,951,641 B2
(45) Date of Patent: Oct. 4, 2005

(54) CONCENTRATED X-RAY CONTRAST MEDIA CAN ACT AS UNIVERSAL ANTIGENS AND CAN INHIBIT OR PREVENT ALLERGIC REACTIONS

(75) Inventor: Elliott C. Lasser, 8081 Calle Del Cielo, La Jolla, CA (US) 92037

(73) Assignee: Elliott C. Lasser, La Jolla, CA (US)

( * ) Notice: Subject to any disclaimer, the term of this patent is extended or adjusted under 35 U.S.C. 154(b) by 0 days.

(21) Appl. No.: 10/821,352

(22) Filed: Apr. 9, 2004

(65) Prior Publication Data

US 2004/0198834 A1 Oct. 7, 2004

Related U.S. Application Data

(63) Continuation of application No. PCT/US02/32467, filed on Oct. 10, 2002.
(60) Provisional application No. 60/329,027, filed on Oct. 12, 2001.

(51) Int. Cl.$^7$ .......................... A61K 49/04; A01N 37/10
(52) U.S. Cl. ...................... 424/9.45; 424/9.45; 424/9.4; 424/9.3; 514/563; 514/568
(58) Field of Search ................................ 424/9.45, 9.4, 424/9.3; 514/563, 568

(56) References Cited

PUBLICATIONS

Roitt et al, Mosby Co, Ltd, 1985, pp. 19.1, 19.7–19.10).*
Bhargava et al. (Drugs of Today, 1998; 34(11), 957–971).*
MacLeod et al (Clin Exp Allergy, 1997;27:1328–1334.*
Brasch, R. et al. "Antibodies to Radiographic Contrast Agents: Induction and Characterization of Rabbit Antibody." *Invest Radiology,* 2: 1–9 (1976).
Carr, D.H. and Walker, A.C. "Contrast media reactions: experimental evidence against the allergy theory." *Br. J. Radiology,* 57: 469–473 (1984).
Dunn, C.R., Lasser, E.C. et al. "Failure to Induce Hypersensitivity Reactions to Opaque Contrast Media Analogs in guinea Pigs." *Invest Radiology,* 10: 317–322 (1975).
Frick, O.L. in *Basic & Clinical Immunology* 2nd Edition, Fudenberg, Stites, Caldwell and Wells editors; Lange Medical Publications; Chapter 22; *Immediate Hypersensitivity* (1976, 1978).
Ishizaka, T. et al. "Biochemical Analysis of Initial Triggering Events of IgE–Mediated Histamine Release from Human Lung Mast Cells." *J Immunology,* 130: 2357–62 (1983).
Katayama, H. et al. "Adverse Reactions to Ionic and Nonionic Contrast Media." *Radiology,* 175: 621–628 (1990).
Krause W., et al. "Physicochemical Parameters of X–Ray Contrast Media." *Invest Radiology,* 29: 72–80 (1994).
Lang, J.H. and Lasser, E.C. "Binding of roentgenographic Contrast Media to Serum Albumin." *Invest Radiology,* 2: 396–400 (1967).

Lasser, E.C. "The Multipotential Pseudoantigenicity of X–Ray Contrast Media." *Int Arch Allergy & Immunol,* 123: 282–290 (2000).
Lasser, E.C. et al. "Reports on Contrast Media Reactions: Analysis of Data from Reports to the U.S. Food and Drug Administration." *Radiology,* 203: 605–610 (1997).
Lasser, E.C. et al. "The Significance of Protein Binding of Contrast Media in Roentgen Diagnosis." *AJR,* 87:338–360 (1962).
Lasser, E.C., Walters, A.J., et al. "Histamin Release by Contrast Media." *Radiology,* 100: 683–686 (1971).
Lasser, E.C. and Lamkin, G.E. "Can Contrast Media Act as 'Pseudoantigens'. " *Academic Radiology.* 5 (suppl. 1): S95–S98 (1998).
Lasser, et al. "A Role for Nitric Oxide in X–Ray Contrast Material Toxicity."*Academic Radiology,* 2: 559–564 (1995).
Lasser EC and Laimkin GE. "Mechanisms of Blood Pressure Change after Bolus Injections of X–ray Contrast Media." *Academic Radiology;* 9 [suppl 1]; S72–S75 (2002).
Myrvik, Q.N. and Weiser, R.S. –*Fundamentals of Immunology,* Second Edition: Lea and Febiger, Philadelphia, Chapter 7, *Interactions of Antigens and Antibodies In Vitro* (1984).
Naminatsu A. et al. "A New Method of the Measurement of Nasal Secretion in Guinea Pigs. " *Int Arch Allergy Appl Immunol.,* 95: 29–34 (1991).
Schneider, P. "Physico–chemical characteristics of isovist–280 and its immunogenic potential." *European Radiology,* 6:15–16 (1996).
Shehadi, W.H. "Adverse Reactions to Intravascularly Administered contrast Media." *AJR,* 124: 145–152 (1975).
Siegle, R.L. and Liebennan, P. "Measurement of Histamine, Complement components and Immune Complexes During Patient Reactions to Iodinated Contrast Material." *Invest Radiology,* 11:98–101 (1976).
Watanabe, N. et al. "In vitro effect of contrast agents during immunoradiometric assay for tumor–associated antigens." *Nucl. Med. Commun.,* 19:63–70 (1998).
Lasser, Elliott C. "The Multipotential Pseudoantingenicity of X–Ray Contrast Media," *Int Arch Allergy Immunol.* 123:282–290 (2000).

* cited by examiner

*Primary Examiner*—Sreeni Padmanabhan
*Assistant Examiner*—Shahnam Sharareh
(74) *Attorney, Agent, or Firm*—Knobbe, Martens, Olson & Bear LLP

(57) ABSTRACT

The present application is directed to the use of X-ray contrast media that act as universal antigens that are labeled herein as "pseudoantigens." X-ray contrast media have the potential to exist in an aggregated state that is greater in increased concentrations. In this aggregated state, contrast media assume the role of multivalent antigens and can successfully compete with any other antigens involved in antibody-antigen reactions that lead to anaphylaxis. In this competition, the large quantity of contrast media serves to inhibit the adverse effects of antibody-antigen reactions without the contrast media itself creating antibodies or creating toxicity problems.

6 Claims, 9 Drawing Sheets

Metrizamide

Iopamidol

Iohexol

Ioxaglate iodixanol
(Visipaque)

FIGS. 8A & 8B
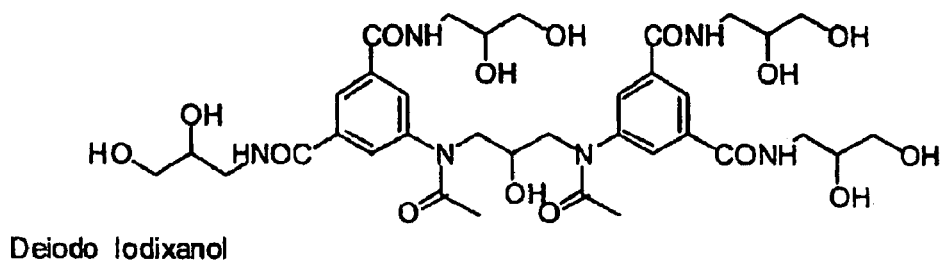
Deiodo Iodixanol
FIG. 8A
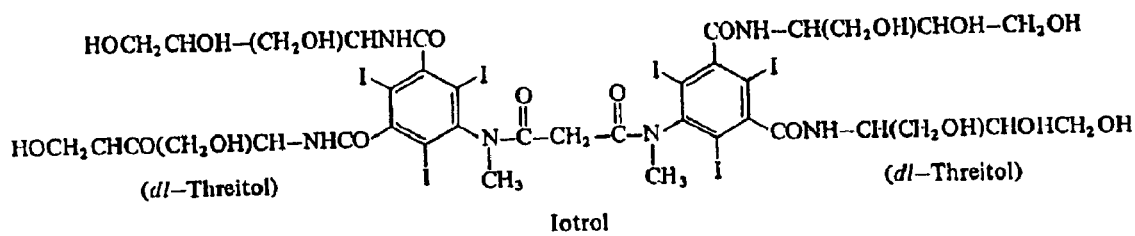
Iotrol
FIG. 8B

CONCENTRATED X-RAY CONTRAST MEDIA CAN ACT AS UNIVERSAL ANTIGENS AND CAN INHIBIT OR PREVENT ALLERGIC REACTIONS

RELATED APPLICATIONS

This patent application is a continuation of PCT Application Ser. No. PCT/US02/32467, filed on Oct. 10, 2002, entitled "Concentrated X-ray Contrast Media Can Act as Universal Antigens and Can Inhibit or Prevent Allergic Reactions," which application claims priority under 35 U.S.C. § 119(e) to U.S. patent application Ser. No. 60/329,027 filed Oct. 12, 2001; both of which are hereby incorporated by reference in their entireties.

BACKGROUND OF THE INVENTION

1. Field of the Invention

The present invention is generally directed to the use of X-ray contrast media to block antigen-antibody complexes. The present invention is more specifically directed to the use of contrast media as drugs to inhibit allergic reactions, to treat or prevent allergic conjunctivitis, allergic rhinitis, their use in "rush" and "routine" immunotherapy and in non-responding anaphylaxis.

2. Description of the Related Art

It has been known for many years that individual X-ray contrast media ("CM") have a varying potential to produce reactions that resemble in every respect the anaphylactic reactions that occur in some individuals subjected to antigens to which they have a known hypersensitivity (Shehadi, W. H., *AJR* 1975, 124, 145–152; Lasser, E. C. et al., *Radiology* 1997, 203, 605–610; Katayama, H. et al., *Radiology* 1990, 175, 621–628). X-ray contrast media reactions, however, occur in individuals regardless of previous exposure, and no one has been able to reliably demonstrate the presence of specific antibodies in these patients or in experimental animals injected with any of the contrast media unless these media were artificially bound to a protein prior to injection (Carr, D. H. and Walker, A. C., *Br. J. Radiology* 1984, 57, 469–473; Brasch, R. et al., *Invest Radiology* 1976, 2, 1–9; Lasser, E. C. et al., *AJR* 1962, 87, 338–360; Dunn, C. R., Lasser, E. C. et al., *Invest Radiology* 1975, 10, 317–322). While previous exposure to contrast media is not necessary for a patient to develop a reaction, reactions occur more commonly in individuals with a history of an allergy of any sort (Katayama, H. et al., *Radiology* 1990, 175, 621–628; Lasser, E. C. et al., *Radiology* 1997, 203, 605–610). Most (non-contrast media) clinical allergic reactions occur when a person is exposed to an antigen having the molecular properties of a protein or of a smaller molecule that can be shown to bind to a protein in vitro (a "hapten"). X-ray contrast media have neither of these attributes. Some out-of-date media demonstrated a degree of binding to some serum proteins, but this was never sufficient to allow the media to act as haptens (Lasser, E. C. et al., *AJR* 1962, 87:338–360). In light of these considerations, the reactions that sometimes occurred after contrast media injections were termed "anaphylactoid" rather than true "anaphylaxis." True "anaphylaxis" is known to require the release of histamine and other mediators present within either mast cells or basophilic cells. The former can be found within tissues while the latter are present in the blood stream. While it could be demonstrated that histamine release occurs in X-ray contrast media reactions (Lasser, E. C., Walters, A. J., et al., *Radiology* 1971, 100, 683–686; Siegle, R. L. and Liebennan, P., *Invest Radiology* 1976, 11:98–101), the exact mechanism by which this occurred has, until recently, been obscure.

Employing a highly sensitive test for antibody-antigen complexing (passive red blood cell hemagglutination inhibition), we found what we consider the answer to this problem. Ovalbumin and gamma globulin (Sigma) were bound to glutaraldehyde stabilized sheep red blood cells (Inter-Cell Technologies, Hopewell, N.J.). Bis-diazotized benzidine was used to bind the ovalbumin to the RBC's. The gamma-globulin bound directly. In both the case of the ovalbumin and the gamma-globulin, the sensitized red blood cells were allowed to incubate with each of the contrast media (methylglucamine iothalamate [CONRAY; 282 mg iodine/ml, Mallinckrodt Medical, St. Louis Mo.], ioversol [OPTIRAY 320; 320 mg iodine/ml, Mallinckrodt], IOXAGLATE [HEXABRIX; 320 mg iodine/ml, Mallinckrodt] and IOTROLAN [ISOVIST; 300 mg iodine/ml, Schering Pharmaceutical; Berlin, Germany]) and the antibodies at room temperature for 2–3 hours prior to evaluation of the potential of the contrast media to compete with the bound ovalbumin or gamma-globulin for their respective antibodies and thereby to function as "pseudoantigens." If no competition occurred, there would be a visible agglutination that covered variable areas of the base of the microtiter well, dependent on the strength of the antibody titer. When competition occurred, there would be a diminished diameter of the agglutination, depending on the antibody titer that could be compared to a control, where saline was substituted for the CM. With complete competition (inhibition), no agglutination would be visible and the RBCs would form a small button of cells at the bottom of the microtiter well. Visible agglutination was evaluated on a 1+ to 4+ basis. Studies were also carried out where the RBCs were incubated with CM before or after binding of the antigen to BDB or the RBC to determine whether competition of the CM with the antigen might actually represent displacement of the CM from the RBC surface.

It was discovered that contrast media can in fact act as an antigen and combine with antibodies (Lasser, E. C. and Lanakin, G. E., *Academic Radiology* 1998, 5 (suppl. 1; S95–S98)). This was shown when, at various concentrations, individual contrast media would inhibit the agglutination of RBC-attached ovalbumin or RBC-attached gamma globulin in the presence of their respective antibodies, thus resulting in a button of cells, rather than agglutination, in the bottom of the microtiter well. Table I shows the results of this experiment.

TABLE I

γ-globulin vs. anti-γ-globulin
Lowest concentration of CM showing a 2+
or 3+ inhibition of 1/500 IgG anti-γ-globulin

|  | mg/ml |
|---|---|
| HEXABRIX | 8.0 |
| ISOVIST | 14.0 |
| OPTIRAY | 16.0 |
| Mga LOTHALAMATE | 28.2 |
| Na LOTHALAMATE | 28.2 |

The results shown in Table I demonstrate that various contrast media compete successfully for binding to the antibodies awaiting the RBC-antigens and thereby rendering the antibodies unavailable to these antigens. Further studies indicated that this occurred most readily in concentrated CM solutions and that most of the contrast media currently in use tend to aggregate to varying degrees and this was particularly true in more concentrated solutions.

Ovalbumin is known to bind on the variable portion of the immunoglobulin molecule (Fab), while gamma globulin is known to bind to the constant portion of the specific immunoglobulin (Fc)(Frick, O. L. in *Basic & Clinical Immunology* 2nd Edition, Fudenberg, Stites, Caldwell and Wells editors; Lange Medical Publications; Chapter 22; *Immediate Hypersensitivity*). Later, the potential of a contrast molecule to compete with ragweed pollen in a ragweed sensitized in vivo rat model (and thereby inhibit the development of ragweed pollen conjunctivitis) was tested. The available data thus far suggests that with local application, the contrast molecule utilized (IODIXANOL; Nycomed, Oslo, Norway) provides a degree of protection by successfully competing with the local application of ragweed antigen and thus inhibiting the potential of the antigen to bind with its specific binding site on anti-ragweed-IgE attached to conjunctival mast cells (see Example V). Thus, it is demonstrated that contrast media have the potential to bind to at least three divergent antibodies and furthermore (inferentially) that binding may take place on either the constant, variable, or both the constant and variable portions of the immunoglobulin molecule.

In the literature, there is a report suggesting that contrast media in vivo reduced the binding of three diverse tumor antigens to their respective antibodies, and thereby falsely lowered the tested blood concentrations of these antigens (Watanabe, N. et al. *Nucl. Med. Commun.* 1998, 19:63–70). The mechanism for this was not explored in the article, but a careful review of the publication demonstrates that it is likely that the various contrast media were interfering with the ability of the tumor antigens to bind to their respective antibodies.

In view of all of the above information, it is believed that contrast media function as totipotential universal antigens and may thereby compete with any antigen for binding sites on its specific antibody.

Since contrast media, like antigens, can bind to antibodies but cannot themselves produce antibodies (unlike antigens), we have termed the contrast media "pseudoantigens." It was noted earlier that the contrast media do not have the chemical characteristics to bind to macromolecules and thus do not have attributes to function like classical antigens. The question then arises: how then, do contrast media compete with antigens? In discussing this issue, it is necessary to have information on the general structure of contrast media molecules.

The X-ray contrast media currently available are generally triiodinated, completely substituted, benzene moieties existing in the form of a monomer or a dimer. These contrast media molecules may be either ionic or nonionic (or in the case of one dimer, part ionic and part nonionic). There are generally slight variations in the amide side chains attached at the 3 and 5 positions on the ring and in the nature of the cations (for the ionic media) and there are slight differences in the length of the aliphatic chains linking the dimers and in the nature of the coupler group.

Some examples of X-ray contrast media that are commercially available are METRIZAMIDE, IOPAMIDOL and IOXEXOL which are nonionic monomers. IOXAGLATE and IOTROLAN are ionic dimers. For purposes of this patent application, only nonionic dimers will be considered. The only two ionic dimers believed to be commercially available thus far are IODIXANOL and IOTROLAN. The term "mammal" as used herein refers to human and non-human mammals. Within certain embodiments of the invention, dosage of CM may be from 0.1–40 grams of CM depending on the subject to be treated and the CM. Other dosages of administered CM may be from 0.01–0.1 grams, 0.1–5 grams, 5–10 grams, 10–15 grams, 15–20 grams, 20–25 grams, 25–30 grams, 30–35 grams, 35–40 grams, 40–45 grams, 45–50 grams and 50–100 grams.

The ability of the contrast media to bind to antibodies must depend on some factor other than their chemical composition since, as noted, their molecular structures do not suggest a potential for binding and in dilute solutions, no binding to globulins could be demonstrated (Lang, J. H. and Lasser, E. C., *Invest Radiology* 1967, 2:396–400). The explanation appears to be the potential of all of the contrast media, in relatively high concentrations, to aggregate, as determined by both physical-chemical analysis, and by comparing theoretical vs. actual osmolalities (Krause W., et al., *Invest Radiology* 1994, 29:72–80; Schneider, P., *European Radiology* 1996, 6:15–16). In an aggregated form, contrast molecules have physical characteristics that simulate a multivalent antigen. In considering the aggregation phenomena it turns out, counter-intuitively, that the best aggregators, and the best antibody binders, are also the contrast media least likely to produce adverse reactions on injection into animals or humans. Under normal circumstances one would expect that the molecule most likely to promote antibody-antigen reactions would be the molecule most likely to play a role in adverse reactions.

In attempting to solve this paradox, a study done much earlier in our laboratory is referenced, wherein dogs injected with a constant volume of contrast media over either a 2 second or 10 second interval consistently produced a higher concentration of histamine release with the longer interval (Lasser, E. C. et al., *Radiology* 1971, 100:683–686).

Histamine release from mast cells and basophils is known to occur when adjacent IgE antibodies attached to these cells are connected by a bridging antigen. Under these circumstances, the receptors that bind the antibodies to the cells are believed to be activated to induce phospholipid methylation and an increase in intracellular cyclic AMP. These biochemical events are followed by an influx of calcium and the release of histamine (Ishizaka, T. et al., *J Immunology* 1983, 130:2357–62). Given these facts, it appeared paradoxical that the faster (2 sec.) injection which should have presented the antibodies on the cells with a higher concentration of contrast media and thus a higher concentration of "pseudoantigens" (and hence greater histamine release) actually resulted in less histamine release than the slower injection.

Further analysis of this paradox pointed to the phenomenon of "antigen-excess." Antigen-excess in vitro has been recognized for many years (Myrvik, Q. N. and Weiser, R. S. —*Fundamentals of Immunology*, Second Edition: Lea and Febiger, Philadelphia 1984, 96102). When a sufficiently concentrated antigen is added to a solution of its specific antibody, there will be successive phases of antibody-excess, antibody-antigen equivalence and finally antigen-excess. In most cases at antibody-antigen equivalence, a precipitate will develop. In antigen-excess, soluble compounds (antigen-antibody complexes) will remain in solution in the supernatant so that precipitation is less than maximal. With a large excess of antigen, inhibition of precipitation may become complete. FIG. 3 depicts our interpretation of the antigen ("pseudoantigen")-excess phenomenon as it applies to CM binding to IgE immunoglobulins on mast cells.

SUMMARY OF THE INVENTION

The present invention is directed to the use of contrast media or modified contrast media molecules (for example contrast molecules with the iodine removed—see FIG. 7B) as drugs that can be utilized to inhibit allergic reactions. The toxicity of the contrast media that is proposed is very low in comparison to almost all drugs on the market and the details of the toxicity of these substances are well known through extensive utilization and research. The contrast media that are proposed are in the dimer and nonionic form and thus are known to be the least toxic of contrast media.

Some possible applications of these "rescue" molecules have been suggested in the body of this application. They will include exploration of their application in human allergic conjunctivitis and in allergic rhinitis. They will also include exploration of their use in status asthmaticus, in "rush" immunotherapy and in routine immunotherapy. A possible use in non-responding cases of anaphylaxis will also be considered. In all of these applications the ability of the contrast molecules to constructively compete with known antigens for their respective antibodies should reduce the number of times when allergic events result in serious consequences. All of this can be accomplished without fear that the contrast molecules will themselves result in the production of antibodies.

Aspects of the present invention are described in the paragraphs below:

1. The use of X-ray contrast media to inhibit, treat or prevent an allergic reaction in a mammal suffering from an allergic reaction by administering X-ray contrast media to such mammal.
2. The use of paragraph 1 wherein the X-ray contrast media inhibits, treats or prevents an allergic reaction by blocking adverse antigen-antibody complex formation.
3. The use of paragraph 1 wherein the X-ray contrast media is selected from the group consisting of dimeric nonionic contrast media or deiodinated nonionic contrast media derivatives.
4. The use of paragraph 1 wherein the X-ray contrast media are in a dimer form.
5. The use of paragraph 1 wherein the X-ray contrast media is non-ionic.
6. The use of paragraph 1 wherein the X-ray contrast media are in an aggregated form.
7. The use of paragraph 1 wherein the X-ray contrast media are administered in a manner selected from the group consisting of subcutaneously, intramuscularly, intravenously or topically.
8. The use of paragraph 1 wherein the X-ray contrast media are triiodinated, completely or partially substituted, benzene moieties existing in the form of a monomer or a dimer.
9. The use of paragraph 1 wherein the antibody is selected from the group consisting of IgA1, IgA2, IgD, IgE, IgG1, IgG2, IgG3, IgG4 and IgM.
10. The use of X-ray contrast media for treating anaphylaxis comprised of the step administering from 0.1 grams to 40 grams of X-ray contrast media to a person suffering from any form or degree of anaphylaxis.
11. The use of paragraph 10 wherein the contrast media is any dimeric nonionic contrast media.
12. The use of paragraph 10 wherein the X-ray contrast media is administered subcutaneously in antigen desensitizing therapy to inhibit local or systemic anaphylaxis resulting from the desensitizing antigen.
13. A method of preventing adverse in vivo antigen-antibody complex formation by administering from 0.1–40 grams of X-ray contrast media to a person.
14. The method of paragraph 13 wherein the X-ray contrast media is selected from the group consisting of dimeric nonionic contrast media.
15. A method of treating or preventing allergic conjunctivitis comprised of the steps of administering from 0.1 to 3 ml of dimeric nonionic X-ray contrast media to an eye suffering from allergic conjunctivitis.
16. The method of paragraph 15 wherein the X-ray contrast media is selected from the group consisting of any dimeric nonionic contrast media.
17. The method of paragraph 16 wherein the X-ray contrast media is selected from the group consisting of IOTROLAN and IODIXANOL.
18. The method of treating allergic rhinitis by administering from 0.1 to 3 ml of a dimeric nonionic contrast media by drop installation into the nose in a mammal suffering from allergic rhinitis or exposed to a known potential nasal allergen.
19. The method of paragraph 18 wherein the X-ray contrast media is a dimeric nonionic CM.
20. The method of paragraph 19 wherein the X-ray contrast media is selected from the group consisting of IOTROLAN and IODIXANOL.

BRIEF DESCRIPTION OF THE DRAWINGS

FIG. 8A shows the structural formula of deiodinated IODIXANOL; and

FIG. 8B shows the structural formula of IOTROL.

DETAILED DESCRIPTION OF THE INVENTION

Figure 1:
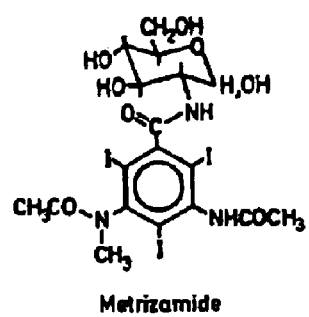
FIG. 1 shows the structures of some commercially available contrast media.
Figure 1:
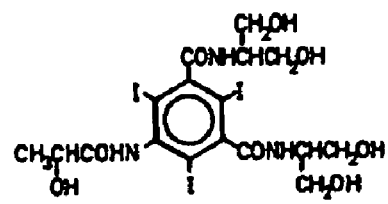
Figure 1:
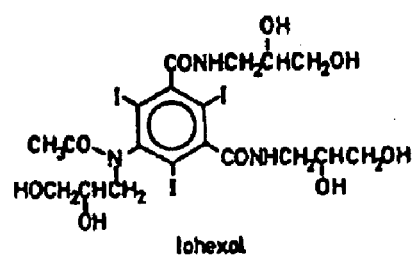
Figure 1:
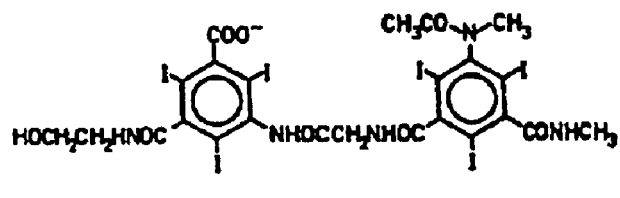
Figure 2A:
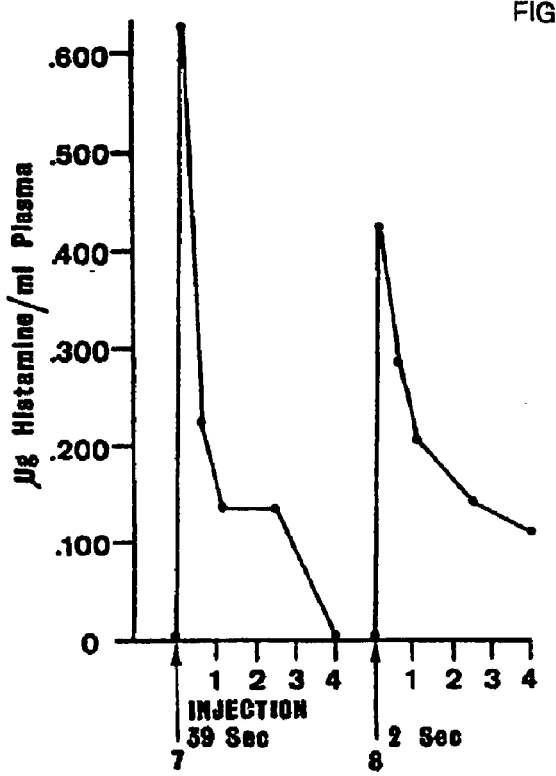
FIGS. 2A–2B show histamine release in response to injections of contrast media.
Figure 2B:
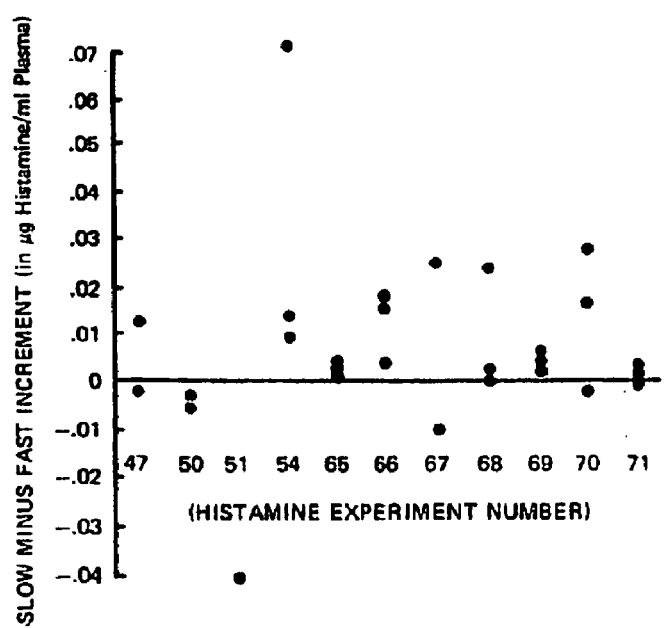
Figure 3:
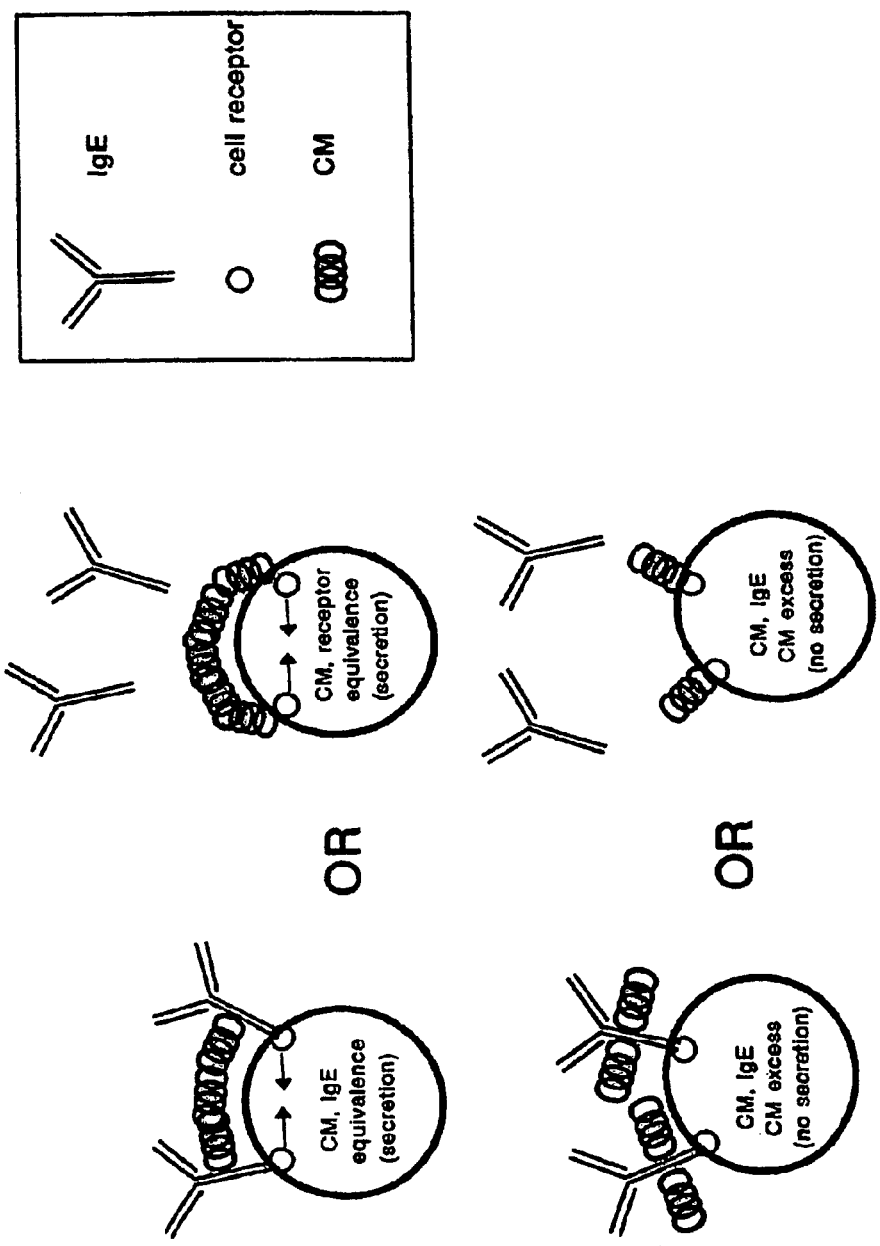
FIG. 3 illustrates the phenomenon of antigen excess.

The phenomenon of antigen-excess has never before been considered in vivo. However, no other intravascular drug is administered at one time in the amount that the contrast media are administered (up to as much as 45 grams in a single injection, etc.). It is believed that the presence of antigens in excess inhibits the likelihood of a single antigen to find empty binding sites on adjacent IgE antibody molecules and thus to produce the release of histamine. An alternative possibility is that the aggregated CM fill the space between adjacent immunoglobulins and prevent the approximation of these molecules and/or their receptors by virtue of steric hindrance. Therefore, the more rapid injection of the contrast media in the dogs is believed to have produced an antigen excess situation relative to the existing IgE antibody on the cells of the dogs from previous sensitization episodes and thus produced less, rather than more, histamine release. Correspondingly, it would no longer appear paradoxical that the contrast media exhibiting the best potential to compete with specific antigens for antibody binding sites in our study of passive hemagglutination inhibition would in fact be the media less likely to produce adverse reactions, rather than the opposite.

Given the above considerations, the question was asked whether contrast media with less potential to compete with antigens in our passive hemagglutination inhibition studies would be more likely to attain antibody-antigen (pseudoantigen) equivalence rather than antigen excess in vivo, and thus be associated with a higher incidence of adverse reactions. This is the case in clinical studies since the ionic monomers, the nonionic monomers, and the nonionic dimers, in that order, needed higher concentrations of concentration-equivalent contrast media to inhibit hemagglutination and range from most toxic to least toxic in the same order. It is thus necessary to consider that the media that are more commonly associated with reactions will be those that are less likely to inhibit hemagglutination in our test and/or are injected in a fashion to produce more dilute contrast solutions.

The significant adverse reactions occurring with contrast media are usually associated with histamine release and a drop in blood pressure. To test the effect on blood pressure in a series of rats, the arterial pressure was monitored following the injection of various contrast media at different concentrations (Lasser, E. C. and Lamkin, G. E. *Academic Radiol,* 2002, 9 [suppl. 1], S72–S75). These studies were done since it is accepted that the release of histamine from mast cells and/or basophils results in a blood pressure lowering effect. Basal endogenous ongoing histamine release thus effects the prevailing blood pressure and events that increase or decrease histamine release will be associated with a decreased or increased blood pressure.

EXAMPLES

Example I

Blood Pressure Changes as an Index of Histamine Release

Sprague Dawley and Brown Norway rats (300–350 g) were purchased from Harlan Sprague Dawley (Indianapolis, Ind.). The CM utilized were meglumine/sodium diatrizoate, an ionic monomer (ANGIOVIST 370; 370 mg I/ml; Berlex Laboratories, Wayne N.J., USA), meglumine iothalamate, an ionic monomer (Conray; 282 mg I/ml; Mallinckrodt Medical, St. Louis, Mo., USA), IOXAGLATE, an ionic dimer (HEXABRIX; 320 mg I/ml; Guerbet Laboratories Aulong-sousBois, France), IOPAMIDOL, a nonionic monomer (ISOVUE 300; 300 mg I/ml; Bracco Pharmaceuticals, Milan, Italy), IOTROLAN, a nonionic dimer (ISOVIST; 300 mg I/ml; Schering Pharmaceuticals, Berlin, Germany), and IOVERSOL, a nonionic monomer (Optiray 240; 240 mg I/ml, Mallinckrodt). The monomers are either ionic or nonionic molecules consisting essentially of a tri-iodinated fully substituted benzene ring. The dimers are two such benzene rings separated by an aliphatic chain. A Propaq blood pressure monitor (Protocol Systems, Beaverton, Oreg., USA) was connected to polyethylene catheters inserted into a carotid artery and measured mean arterial pressures. Injection rates into a tail vein varied from 2 to 8 ml/kg/min. Modifications of the mean blood pressure tracings in individual animals were studied by injections of the following substances either preceding or following the CM. NG-nitro-L-arginine methyl ester (L-NAME; Sigma), sodium nitroprusside (SNP; Sigma), histamine (Sigma), phenylephrine (Sigma), phentolamine; (Sigma), L-arginine (Sigma), diphenhydramine (Benadryl; Sigma), and BQ 123 (American Peptide Co., Sunnyvale, Calif., USA).

Figure 4A:
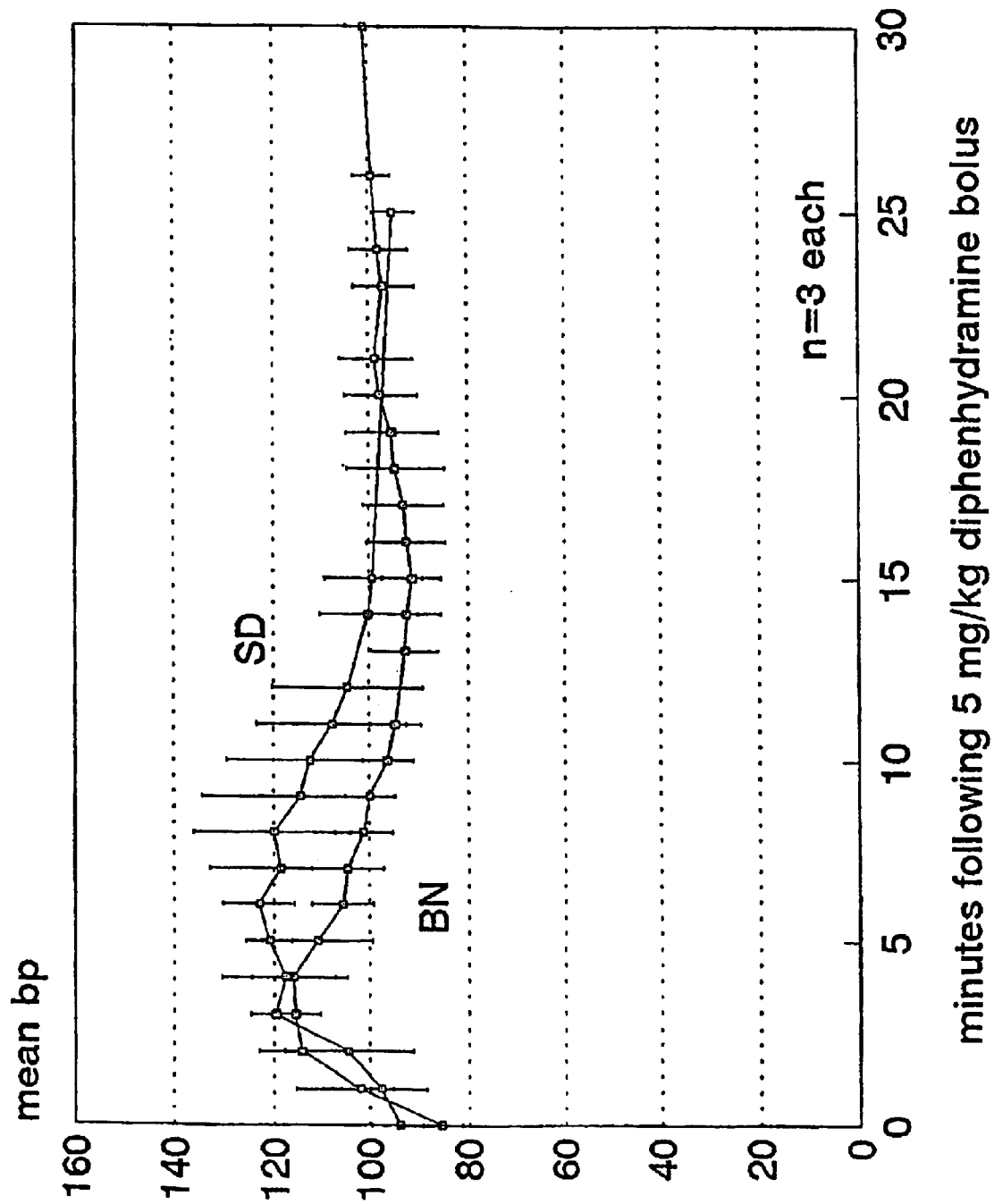
FIG. 4A shows the rise in blood pressure in Brown-Norway and Sprague Dawley rats following the bolus injection of 5 mg/kg of diphenhydramine.
Figure 4B:
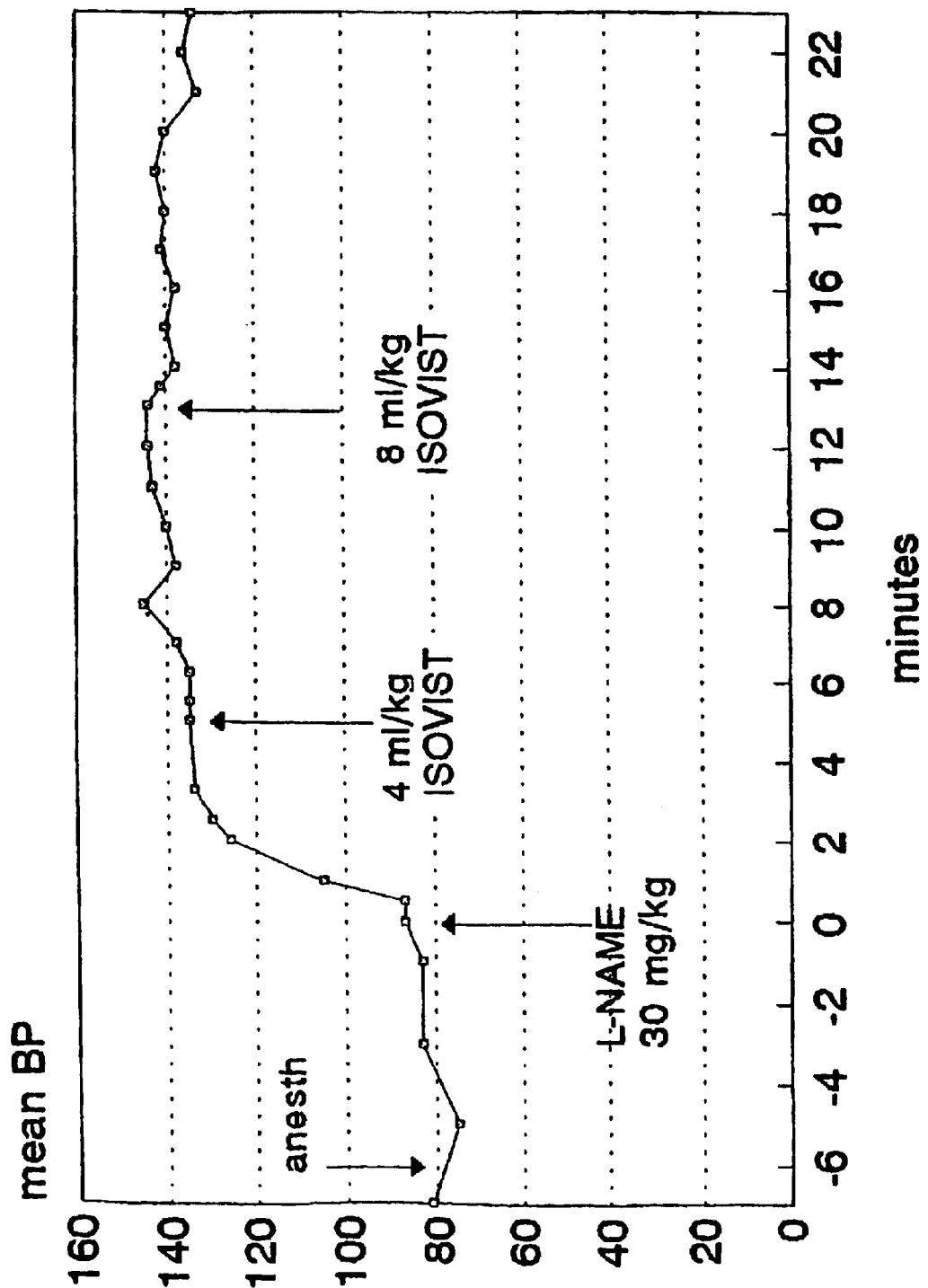
FIG. 4B shows that in 15 tested animals, injection of L-Name, a nitric oxide inhibitor, produces a rise in BP and that ISOVIST no longer produces a rise in blood pressure when the production of nitric oxide is blocked.

FIG. 4A shows that the infusion of an H-1 blocker (diphenhydramine) in the rats produced an immediate elevation in blood pressure. The injection of L-NAME, the L-arginine analog that blocks the production of nitric oxide, also produced an immediate elevation in blood pressure (FIG. 4B). It is also worth noting that the injection of a nonionic contrast media dimer (ISOVIST), when injected by itself, produces an elevation in pressure, can no longer produce an elevation in blood pressure when the production of nitric oxide is blocked. This is evidently due to the fact that the dimer elevates pressure by blocking ongoing IgE mediated histamine/nitric oxide release and hence their vascular dilating effect, but can not evidence this when nitric oxide release is already blocked. The results of Example I are described below in Table II.

TABLE II

Net increase/decrease in mean arterial blood pressures in the Brown-Norway and Sprague Dawley rats are summarized below

| Contrast media: | Brown Norway Rats mm Hg (mean ± S.E.) | Sprague Dawley Rats mm Hg (mean ± S.E.) |
|---|---|---|
| Monomers (4 ml) | | |
| Conray | decrease (37 ± 1.6) (3) | decrease (55 ± 5.0) (3) |
| Optiray | decrease (20 ± 1.5) (3) | NO DATA |
| Monomers (8 ml) | | |
| Isovue | decrease (36 ± 8.6) (2) | decrease (27 ± 8.6) (2) |
| Optiray | decrease (33 ± 2.8) (3) | decrease (22 ± 0.0) (1) |
| Angiovist | decrease (40 ± 0.0) (1) | NO DATA |
| Dimers (4 ml) | | |
| Isovist | increase (18 ± 0.00) (1) | NO DATA |
| Dimers (8 ml) | | |
| Isovist | increase (20 ± 2.0) (4) | increase (11 ± 4.6) (3) |
| Hexabrix | increase (31 ± 4.6) (3) | NO DATA |

As the above results demonstrate, monomers produced a net fall in blood pressure while the dimers produced a net elevation of blood pressure. In most experimental and clinical studies, CM injections have been associated with a reduction in blood pressure so it came as no surprise that the monomers produced a net fall in blood pressure. The fact that dimers produced a net elevation in blood pressure was a surprise and was contrary to expectations.

In attempting to understand why a blood pressure elevation was obtained under our experimental circumstances it was considered what would happen to blood pressure in these animals if the histamine receptor (H-1 receptor) was blocked. It was found that this consistently produced a pressure elevation lasting about 20 minutes (see FIGS. 4A–4B). In another publication, it was noted that nitric oxide, as a mediator released by histamine through activity at the H-1 receptor, played a role in lethal dose studies in rats and that blocking the production of nitric oxide increased the amount of contrast that a rat could accept before lethality (Lasser, et al., *Academic Radiology* 1995, 2, 559–564). When the production of nitric oxide was blocked (utilizing L-NAME, a nitric oxide analog), a blood pressure elevation was produced similar in all respects to that produced by blocking the H-1 receptor (see FIGS. 4A and 4B). The same findings occurred in the presence of salient blood pressure modifiers (phenylephrine and phentolamine) (Lasser E C and Lainkin G E Academic Radiology 2002; 9 [suppl 1]; S72–S75). Since, as noted, injections of the dimers produced blood pressure elevations and these could be blocked by L-NAME, it was concluded that the blood pressure elevations in these circumstances were due to an antigen (pseudoantigen) excess effect that effected (inhibited) endogenous ongoing histamine and nitric oxide release resulting from endogenous antigens interacting with their specific IgE antibodies on mast cells and basophils.

Example II

Effect of Dimeric CM on Blood Pressure Changes in Anaphylaxis

To further substantiate the concept that contrast media, acting as pseudoantigens, could interfere with existing antigen-antibody reactions, an experiment was conducted where a series of rats were sensitized to ovalbumin and later challenged the rats by intravenous injections of ovalbumin.

Varying CM or other materials were injected into the tail vein of anesthetized Sprague Dawley rats (300–400 mg). The CM tested were IOXAGLATE and IODIXANOL. Both are CM dimers and IOXAGLATE is ionic and IODIXANOL is nonionic. The CM injections were done 12 to 14 days after sensitization of the rats by intraperitoneal injections of 1 mg of ovalbumin in normal saline. A Propaq blood pressure apparatus was connected to polyethylene catheters inserted into a carotid artery to monitor mean arterial blood pressure. Injection rates were 6 ml/kg/min. The CM were injected I.V. either 6 hours before, 45 minutes before, concurrent with, or 10 minutes post challenge of a dose of 10 mg of ovalbumin. Saline injections, equiosmolar to the CM and injected at the same time intervals served as controls.

Figure 5:
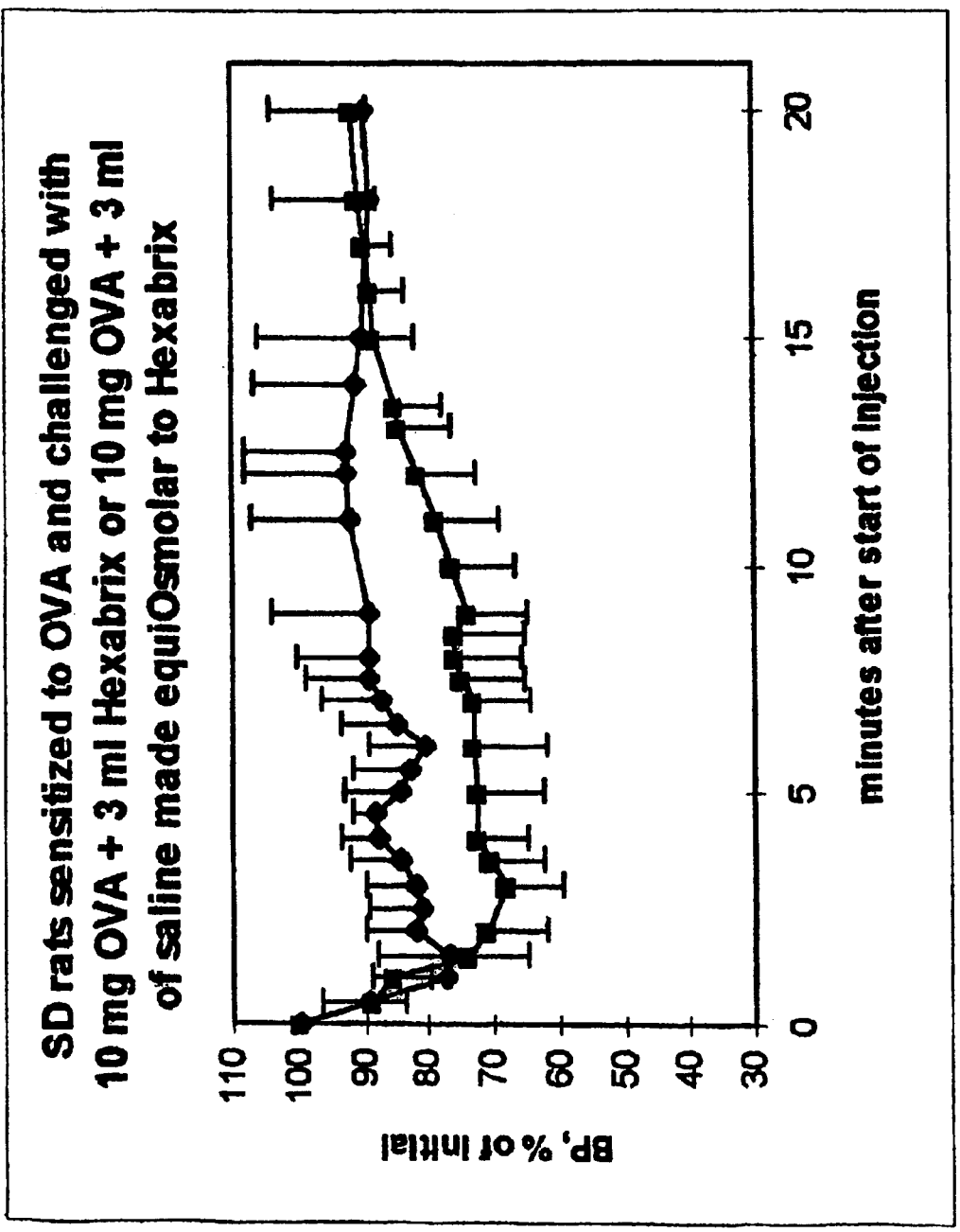
FIG. 5 shows that the injection of a CM dimer along with OVA in 5 OVA-sensitized rats (diamonds) diminishes the prolonged fall in blood pressure that results from injection of OVA and saline made equiosmolar to the dimer in 4 sensitized rats (squares) which results from antigen-specific, antigen equivalent immunogenic mechanisms having to compete with the pseudoantigen, antigen excess mechanisms operative when the CM accompanies the OVA.
Figure 6:
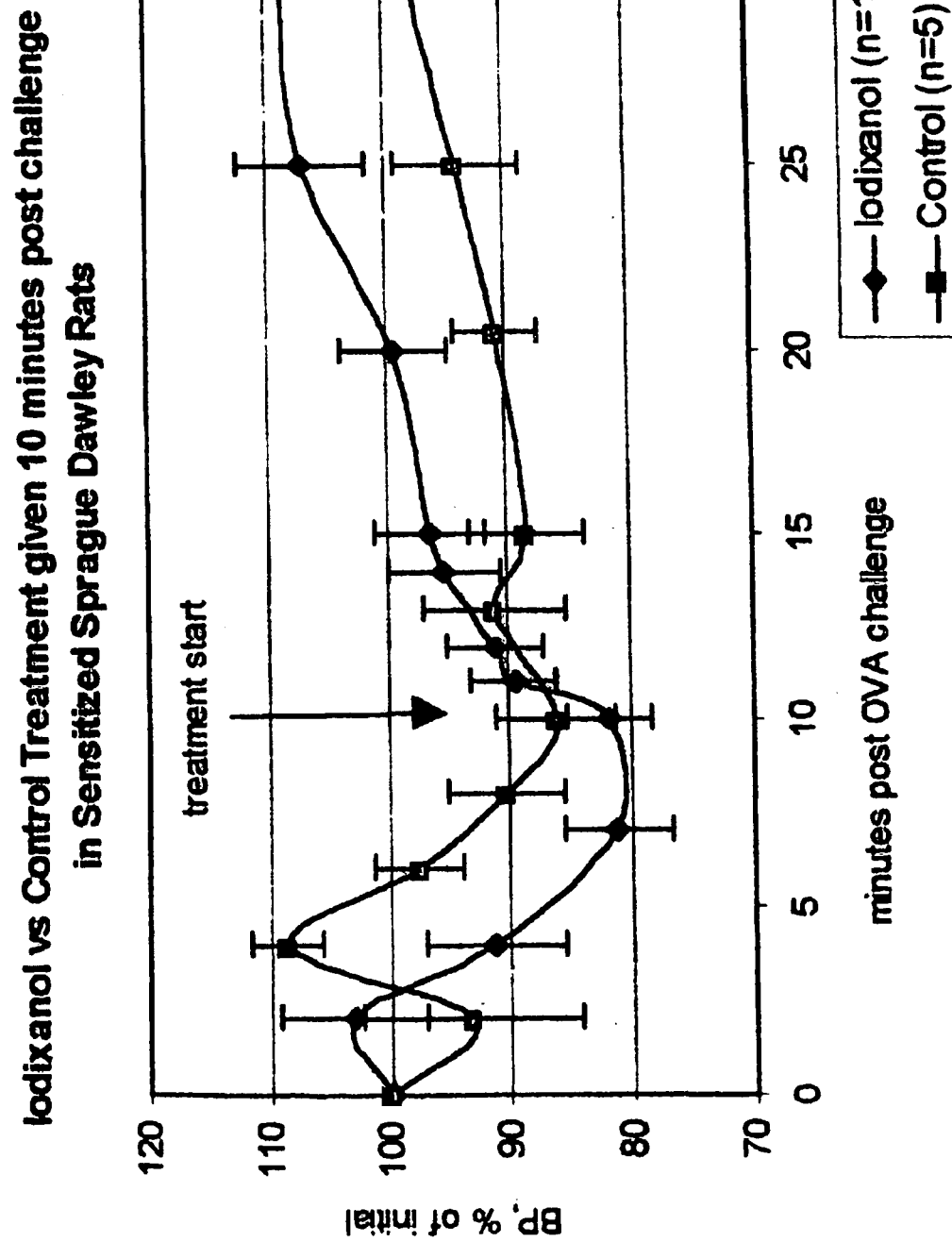
FIG. 6 shows IODIXANOL vs. control treatment given 10 minutes post challenge in sensitized Sprague Dawley rats.
Figure 7:
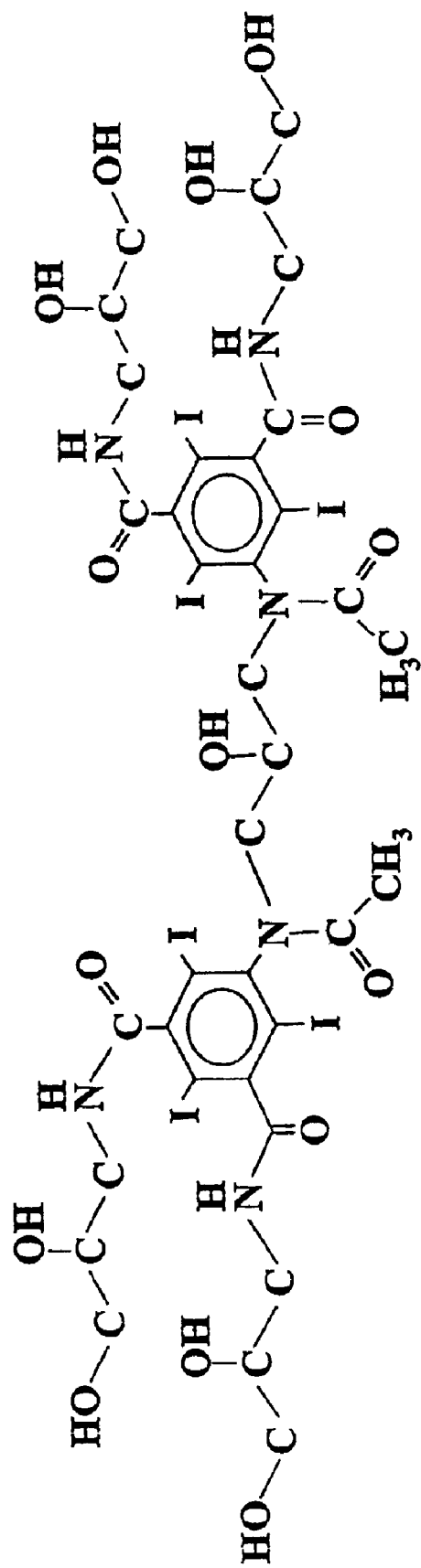
FIG. 7 shows the structural formula IODIXANOL.

In the absence of contrast media the ovalbumin injections invariably resulted in a fall in blood pressure (anaphylactic shock) that reached a nadir at about 10 minutes and remained at this level, or slowly rose towards normal. When these studies were repeated in the presence of a contrast media dimer (IODIXANOL or IOXAGLATE) or equiosmolar saline, the contrast media, injected 6 hours before, 45 minutes before, concurrently, or 10 minutes after the ovalbumin contrast media produced a more rapid return of the blood pressure to normal levels than did the saline (FIG. 5 shows blood pressure tracings when the C.M. and Ovalbumin were injected concurrently and FIG. 6 shows effect when the Ovalbumin and C.M. were injected 10 minutes after the BP nadir).

Example III

Effects of Monomeric or Dimeric Nonionic CM on Lethality of Ionic Media

The concept was also tested by examining the potential of a monomer nonionic contrast and a dimer nonionic contrast to diminish the lethality in 300–350 g Sprague-Dawley rats of an ionic monomer CM. The nonionic monomer used was IOVERSOL (Optiray 160, Mallinckrodt; St Louis Mo.). The nonionic dimer used was IOTROLAN (Isovist, Schering, Berlin, Germany). The ionic contrast media used was 70% methylglucamine iothalamate (Conray, Mallinckrodt; St Louis Mo.). An LD-100 technique was used to determine lethality. This technique involves an immediate decision on mortality and is more humane than the LD-50 technique since the animals do not undergo post technique morbidity for variable periods. The determination of death in this technique is done by a continuous I.V. infusion of CM and noting at what dose the animal suspended respirations for a period of at least 15 seconds. For CM toxicity studies the technique correlated well with published data using a standard LD-50 technique.

The results below shows that replacing 30% saline with 30% C.M. (nonionic) actually lowers mortality rather than increasing it. Example III demonstrates that when either the monomer nonionic or the dimer nonionic, both of which exhibit stronger binding potential to immunoglobulins than does the ionic monomer used, are substituted for saline, the lethality of the mixture diminishes (the animals can accept more total contrast media before lethality). This can now be assumed to be due to the nonionic CM partially blocking the effect of the ionic media on IgE immunoglobulins and mast cell release.

| | | $LD_{100}$ | P |
|---|---|---|---|
| 1) | 30% OPTIRAY (nonionic) & 70% CONRAY (ionic) | 22.2 ± 1.9 (3) | .003 |
| 2) | 30% Saline* & 70% CONRAY | 16.4 ± 0.8 (4) | |
| 3) | 30% ISOVIST (nonionic) & 70% CONRAY (ionic) | 23.7 ± 1.4 (3) | .01 |
| 4) | 30% Saline* & 70% CONRAY | 17.9 ± 1.7 (3) | |

*Saline equiosmolar to OPTIRAY or ISOVIST

Example IV

Passive Cutaneous Anaphylaxis

In a further test of the ability of appropriate contrast media to mitigate ongoing antigen-antibody reactions, a passive cutaneous anaphylaxis (PCA) experiment was performed in rats.

In this Example, rats were injected intradermally with 50 μL of serum from ovalbumin sensitized rats and varying mixtures of Na/meglumine iothalamate (MD-76; 370 mg iodine/ml, Mallinckrodt) and normal saline to a total of 50 μl. This was followed in 5–7 hours by intravenous injections of 1 mg ovalbumin along with Evans Blue and then measurement of the subsequent extravasation of the blue coloring in the area under the skin. Evans Blue binds to serum albumin and the diameter of the area of blue indicates extravasation of albumin secondary to specific antigen-antibody reactions. The experiment showed that dilute intradermal concentrations of the contrast media appeared to accentuate the permeability change, whereas concentrations greater than 20% progressively inhibited the permeability (presumably by "pseudoantigen" excess). In this case, where large amounts of CM are available due to local deposition, even an ionic monomer was sufficient to block specific antibody-antigen reactivity (see Table III below).

TABLE III

Passive Cutaneous Anaphylaxis

| Site # | μl CM | μl Saline | μl Sensitized serum | Stain (mm ± S.E./10) |
|---|---|---|---|---|
| 1 | 50 | 0 | 50 | 7.5 ± 7 |
| 2 | 40 | 10 | 50 | 10.0 ± 10 |
| 3 | 30 | 20 | 50 | 17.5 ± 10 |
| 4 | 20 | 30 | 50 | 62.5 ± 28 |

TABLE III-continued

Passive Cutaneous Anaphylaxis

| Site # | μl CM | μl Saline | μl Sensitized serum | Stain (mm ± S.E./10) |
|---|---|---|---|---|
| 5 | 10 | 40 | 50 | 115 ± 60 |
| 6 | 0 | 50 | 50 | 87.5 ± 31 |

Controls with nonsensitized serum (3 rats) and 0, 25, and 50 μl CM showed no stain. Controls (4 rats) with sensitized serum and 1.9% saline replacing CM produced no stain at site 1, and 55 mm and 50 mm stains at sites 3 and 5. Other sites were not tested.

Significant differences (Student t-test): 2 vs. 4 (0.004), 2 vs. 5 (0.0002), 2 vs.6 (0.00004)

Example V

Protective Effects of CM on Experimental Allergic Conjunctivitis

In this Example, the potential protective effect of a contrast material on experimental allergic conjunctivitis induced in rats was examined. The rats were sensitized systemically to either ovalbumin or ragweed pollen and 10 to 12 days later obtained local senitization by several applications of the respective antigens to the eyes. The rats were then challenged with a larger dose of the antigen accompanied by either the contrast media or equiosmolal saline and sacrificed at several different time periods for examination of the excised eyes.

The most reliable indicator of conjunctivitis was found to be a cellular infiltration in the conjunctiva and/or in the underlying lamina propria. The tissues were examined on a "blinded" basis and assigned a 0 to 3+ rating based on the perceived abundance of inflammatory cells (mostly lymphocytes, but also including eosinophils, polymorphonuclear leukocytes, and mast cells). The ovalbumin experiment was carried out at 3 hours post antigen application (8 rats) and at 24 hours post application (8 rats) and the ragweed study was carried out at 1 hour post application (8 rats) and at 24 hours post application (8 rats). The cumulative scores for the ratings in each set of rats were recorded. Details of the ovalbumin study are as follows.

16 male Sprague-Dawley rats (approximately six weeks old) were given IP injections of 1 ml of 1 mg/ml ovalbumin (Sigma) in normal saline, containing 20 mg alum (Sigma) on Day 1 and on Day 2. On Day 11, 10 μl of DTT (a dispersing agent) (Sigma) at 1 M in saline was applied to both eyes, followed by 20 μl of saline to the control (left) eye and 20 μl of IODIXANOL (Nycomed; Oslo, Norway). 15 minutes later, both eyes were treated with DTT and then ovalbumin (20 μl of 1 mg/ml ovalbumin in saline). This process was done four times at 15 minute intervals. The interval between DTT and treatments was approximately 3–5 min. for each rat. 8 rats were observed for 3 hours afterwards and 8 for 24 hours.

RESULTS OVALBUMIN SENSITIZED RATS

| 2 HOUR READING: | | 24 HOUR READING | |
|---|---|---|---|
| saline + ovalbumin | 8+ | saline + ovalbumin | 11+ |
| CM + ovalbumin | 1+ | CM + ovalbumin | 5+ |

A ragweed pollen experiment also involved 16 Sprague-Dawley rats born approximately 2 months previously and sensitized on Day 1 with SQ injections of 0.1 ml of N. saline containing 100 μg of ragweed pollen (P-0146, Sigma) and 20 mg alum. On Day 14, 20 μl of saline (left eye) or 20 μl of IODIXANOL (right eye) were applied to the eyes. 15 min. later, both eyes were treated with 10 μl of phosphate buffered saline containing 1.5 mg of ragweed pollen. The process was done 4 times at 15 min. intervals. 8 rats were observed for 1 hour preceding sacrifice and 8 for 24 hours.

RESULTS RAGWEED POLLEN SENSITIZED RATS

| 1 HOUR READING: | | 24 HOUR READING | |
|---|---|---|---|
| saline + ragweed | 0 | saline + ragweed | 15+ |
| CM + ragweed | 0 | CM + ragweed | 8+ |

It was also of interest that there were no absolute zeros in the saline group while there were 3 zeros in the IODIXANOL group and the only 3+ scores recorded were in the saline group. For the combined ovalbumin and ragweed pollen 24 hour studies, the CM differed from saline by P=0.068 (Student two tailed t-test).

Example 6

Protective Effects of Contrast Media on Allergic Rhinitis

Sprague Dawley rats were given an IP injection of 1 ml of 1 mg/ml ovalbumin in normal saline containing 20 mg alum (reconstituted aluminum hydroxide gel). 10 days later, 8 of the rats were given 20 μl of saline made equiosmolal to IODIXANOL into both nostrils via a small catheter placed just inside the nostril and 8 rats were given 20 μl of IODIXANOL into both nostrils. 15 minutes later, the animals were challenged locally by installation of 20 μl of 1 mg/ml ovalbumin via the catheter into each nostril.

The animals were then available to test for the quantity of secretion escaping from each nostril utilizing the method described by Namimatsu A. et al. (*A New Method of the Measurement of Nasal Secretion in Guinea Pig, Int Arch Allergy Appl Immunol* 1991, 95, 29–34) which is hereby incorporated by reference. In this method, a piece of cotton thread dyed with fluorescein at one end is inserted into the anterior end of the nostril and kept there for 60 seconds. The stretch of color resulting will be proportional to the fluid volume of the secretion as will be the increase of weight of the thread. It is expected that the noses pretreated with the IODIXANOL will show significantly less secretion with this model than will the noses pretreated with saline. For example, it is expected that the noses pretreated with saline will show a stretch of color averaging about 20 to 40 mm while the noses pretreated with IODIXANOL will probably average 10 to 20 mm, reflecting the inhibition of the locally applied allergen due to the antigen-excess phenomenon of the CM.

Similar studies will be carried out to examine the cellular changes resulting when the animals are pretreated and challenged as above, except that the pretreatment and challenge will be carried out for a period of 3 days. 24 hours later the animals will be sacrificed. The head of each rat will be removed and fixed in formalin for 3 days and then decalcified (5% trichloroacetic acid for 5 days). The nasal septal mucosa will then be examined for eosinophilic infiltration. It is expected that the rats receiving the IODIXANOL pretreatment preceding ovalbumin challenge for each of the 3 days will exhibit less eosinophilic infiltration in the mucosal tissues than will the rats pretreated with saline. For example, it is expected that the saline pretreatment will show an average of about 40–60 eosinophils/oil immersion objective field counted on both sides of the septal cartilage while the IODIXANOL pretreatment group will show a much smaller average. In the nasal areas as in most other tissues in the body, the infiltration of eosinophils is an index of a hypersensitivity response.

From all the above experimental results, it is concluded that X-ray contrast media, to varying degrees, have the potential to serve as universal antigens that we have labeled "pseudoantigens." This property appears to derive from the fact that all of the contrast media have the potential to exist in an aggregated state that is greater in increased concentrations. In this aggregated state, contrast media assume the role of multivalent antigens and can successfully compete with, and thus inhibit, any other antigens involved in antibody-antigen reactions that might lead to anaphylaxis. In this competition, the large quantity of contrast media that can be made available enables the media to function in an antigen-excess mode that then inhibits the adverse effects which would otherwise result from the specific antibody-antigen reaction.

What is claimed is:

1. A method of treating allergic conjunctivitis comprising the step of administering from 0.1 to 3 ml of a dimeric nonionic X-ray contrast media selected from triiodinated, completely or partially substituted, benzene moieties existing in the form of a dimer, to an eye of a mammal suffering allergic conjunctivtis.

2. The method of claim 1 wherein the X-ray contrast media is selected from the group consisting of IOTROLAN and IODIXANOL.

3. A method of treating allergic rhinitis comprising administering from 0.1 to 3 ml of a dimeric nonionic X-ray contrast media selected from triiodinated, completely or partially substituted, benzene moieties existing in the form of a dimer, into the nose in a mammal suffering from allergic rhinitis.

4. The method of claim 3, wherein the X-ray contrast media is selected from the group consisting of IOTROLAN and IODIXANOL.

5. The method of claim 4, wherein the X-ray contrast media is IODIXANOL.

6. The method of claim 2, wherein the X-ray contrast media is IODIXANOL.

* * * * *

UNITED STATES PATENT AND TRADEMARK OFFICE
CERTIFICATE OF CORRECTION

PATENT NO. : 6,951,641 B2 Page 1 of 1
APPLICATION NO. : 10/821352
DATED : October 4, 2005
INVENTOR(S) : Elliott C. Lasser It is certified that error appears in the above-identified patent and that said Letters Patent is hereby corrected as shown below:

Title Page; item (56);

On page 1, in column 1 at line 1, delete "Roitt et al," and insert --Roitt et al.,--, therefor.

On page 1, in column 1 at line 1, delete "Mosby Co, Ltd" and insert --Mosby Co., Ltd.--, therefor.

On page 1, in column 1 at line 3, delete "MacLeod et al" and insert --MacLeod et al.--, therefor.

On page 1, in column 2 at line 23, delete "Naminatsu" and insert --Namimatsu--, therefor.

On page 1, in column 2 at line 36, delete "tumor" and insert --tumour--, therefor.

In column 10 at line 20, below "release." insert --S.D. Rats – $LD_{100}$ (gl/kg)--.

In column 11 at line 33, delete "senitization" and insert --sensitization--, therefor.

In column 14 at line 11, in Claim 1, after "suffering" insert --from--.

In column 14 at line 12, in Claim 1, delete "conjunctivtis" and insert --conjunctivitis--, therefor.

Signed and Sealed this

First Day of June, 2010

David J. Kappos
*Director of the United States Patent and Trademark Office*